United States Patent
Dorfmueller et al.

(10) Patent No.: US 8,182,665 B2
(45) Date of Patent: May 22, 2012

(54) SENSOR ELEMENT FOR GAS SENSORS AND METHOD FOR OPERATING SAME

(75) Inventors: Lutz Dorfmueller, Gerlingen (DE); Sabine Roesch, Ditzingen (DE); Detlef Heimann, Gerlingen (DE); Stefan Rodewald, Yokohama (JP); Helmut Marx, Hochdorf (DE); Henrico Runge, Stuttgart (DE); Harald Guenschel, Gerach (DE); Ralf Schmidt, Gerlingen (DE); Markus Siebert, Leonberg (DE); Lothar Diehl, Gerlingen (DE); Thorsten Ochs, Schwieberdingen (DE); Juergen Sindel, Farmington Hills, MI (US); Juergen Ruth, Stuttgart (DE); Andreas Schaak, Winnenden (DE); Henrik Schittenhelm, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 560 days.

(21) Appl. No.: 12/084,675

(22) PCT Filed: Oct. 20, 2006

(86) PCT No.: PCT/EP2006/067608
§ 371 (c)(1),
(2), (4) Date: May 6, 2008

(87) PCT Pub. No.: WO2007/054424
PCT Pub. Date: May 18, 2007

(65) Prior Publication Data
US 2009/0217737 A1    Sep. 3, 2009

(30) Foreign Application Priority Data
Nov. 8, 2005 (DE) .................. 10 2005 053 120

(51) Int. Cl.
*G01N 27/27* (2006.01)
(52) U.S. Cl. .............. 204/426; 204/424; 73/23.31
(58) Field of Classification Search ............ 95/283; 204/424, 426; 205/784.5, 785
See application file for complete search history.

(56) References Cited

U.S. PATENT DOCUMENTS

| | | | |
|---|---|---|---|
| 4,649,364 A | 3/1987 | Tanahashi et al. | |
| 2003/0196499 A1* | 10/2003 | Bosch et al. | 73/865.5 |
| 2008/0048681 A1* | 2/2008 | Birkhofer et al. | 324/693 |

FOREIGN PATENT DOCUMENTS

| | | |
|---|---|---|
| DE | 198 51 966 | 5/2000 |
| DE | 103 31 838 | 9/2004 |
| DE | 10 2005 003118 | 10/2007 |
| JP | 57 110948 | 7/1982 |
| WO | 2005/093233 | 10/2005 |
| WO | WO 2006077197 A1 * | 7/2006 |

OTHER PUBLICATIONS

English translation of JP57110948A. Translation date: Apr. 2011.*

* cited by examiner

*Primary Examiner* — Lisa Caputo
*Assistant Examiner* — Punam Roy
(74) *Attorney, Agent, or Firm* — Kenyon & Kenyon LLP

(57) ABSTRACT

A sensor element is provided for gas sensors, in particular to determine particles in gas mixtures, the sensor element including at least one electrochemical measuring element exposed to the gas mixture to be determined, and at least one temperature-measuring element integrated into the sensor element. The temperature-measuring element includes a resistor track, which has an electric resistance of less than 180 Ohm at 0° C. The resistor track may thus be produced by thin-foil technology, such as screen printing, for example.

12 Claims, 5 Drawing Sheets

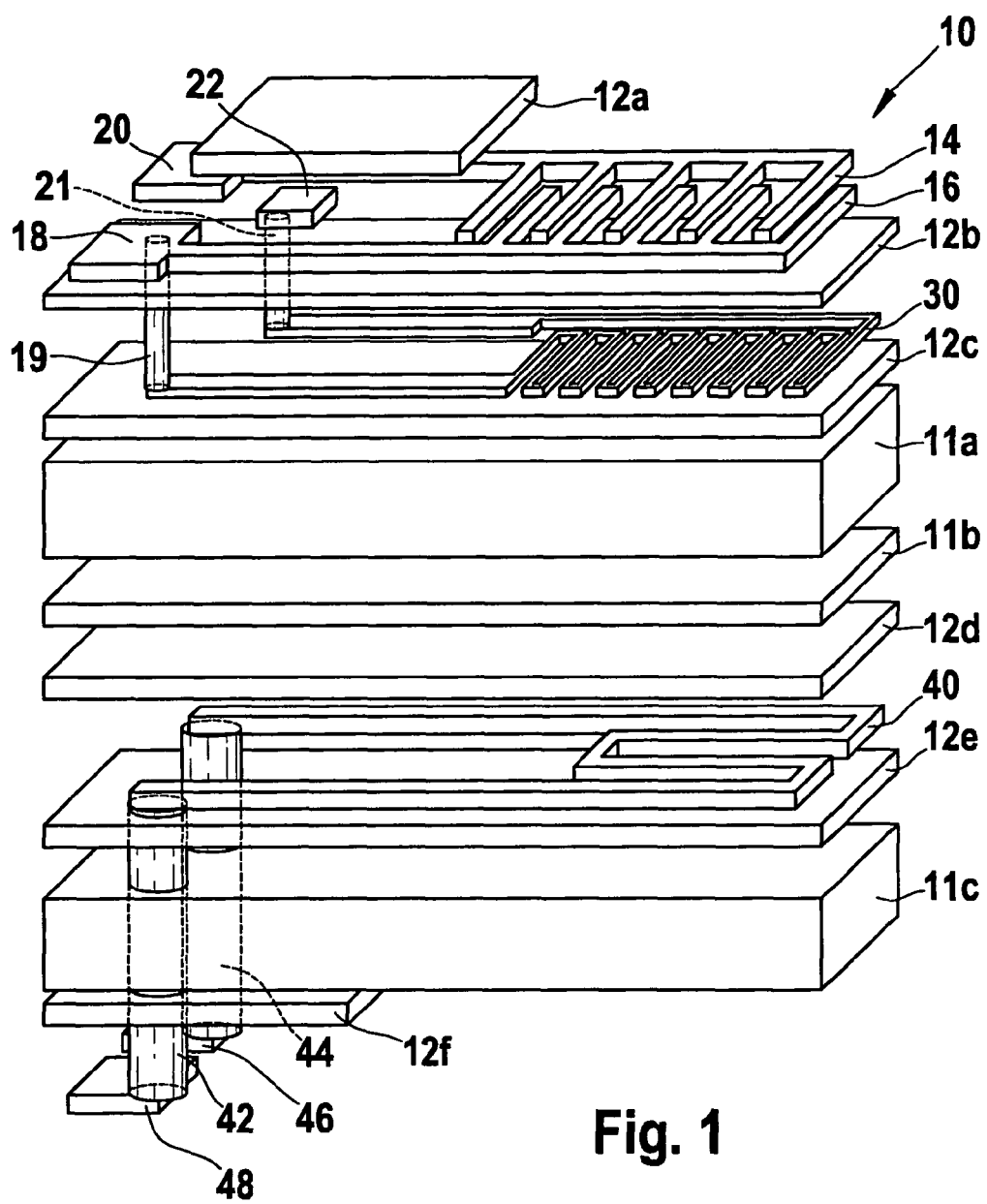
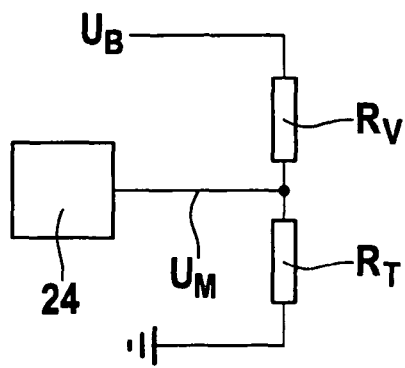
Fig. 1
Fig. 2

SENSOR ELEMENT FOR GAS SENSORS AND METHOD FOR OPERATING SAME

FIELD OF THE INVENTION

The present invention is based on a sensor element, a gas sensor containing same, a method for determining particles in gas mixtures, and their use.

BACKGROUND INFORMATION

The testing or monitoring of the reliability of exhaust gas aftertreatment systems currently used in motor vehicles requires sensors by which the particle concentration in the combustion exhaust gas can be ascertained precisely, even during long-term operation. In addition, the use of such sensors should enable a loading prognosis of, for instance, a diesel particulate filter installed in an exhaust gas system, in order to attain a high degree of system safety and thereby allow the use of more cost-effective filter materials.

A sensor for detecting particles in a fluid flow is discussed in DE 10 2005 003118, the sensor being developed on the basis of a ceramic multi-layer substrate. It includes two measuring electrodes, set apart from one another, which are exposed to the combustion exhaust gas that is to be tested. If soot is depositing between the two measuring electrodes, this will produce a current flow between the measuring electrodes when a voltage is applied to the measuring electrodes. A heating element, designed in the form of layers, makes it possible to rid the electrodes and their surroundings of deposited soot particles via a thermal process. The sensor also includes a temperature-measuring element that can detect the temperature of the sensor. The heating element is located within the layer composite of the sensor, between the temperature-measuring element and the measuring electrodes. A disadvantage of such a structure of the sensor is that conventional temperature-measuring elements of ceramic sensors have resistor tracks that exhibit increased electric resistance, which can be produced only by complicated production methods such as photo fine-structuring methods, for example.

SUMMARY OF THE INVENTION

It is an object of the exemplary embodiments and/or exemplary methods of the present invention to provide a sensor element for sensors, and a method for determining the concentration of particles in gas mixtures, which permit an accurate temperature regulation and yet may be produced in a cost-effective manner.

The sensor element, the gas sensor and the method having the characterizing features of the respective independent claims provide the advantage that the object on which the exemplary embodiments and/or exemplary methods of the present invention is based is attained in an advantageous manner. This is specifically due to the fact that a sensor element having a simple structure is able to be utilized, and that a temperature-measuring element integrated into the sensor element is able to be realized in an especially cost-effective manner.

Since the temperature-measuring element has a resistor track that exhibits relatively low electric resistance, it is easily implementable on a ceramic substrate of the sensor element using what is referred to as thick-film technology, whereas conventional temperature-measuring elements realized in ceramic gas sensors have higher electric resistance and require their resistor track to be produced in a complex manner via thin-film technology.

Further advantageous specific embodiments of the present sensor element, gas sensor, and method for operating such are described herein.

It is advantageous, for instance, if the temperature-measuring element includes a resistor track, which has track regions that are bridged by burn-up segments. In this way, it is especially easy to adjust the temperature-measuring element following its production because an interruption of the electrically conductive burn-up segments via the supply of energy results in an actual extension of the resistor track and thus leads to an increase in its total resistance.

In another advantageous specific embodiment, a measuring electrode of an electrochemical measuring element integrated into the sensor element is additionally at least regionally implemented as resistor track of the temperature-measuring element or as resistor track of a heating element. This reduces the number of terminal contacts required to control the sensor element. Thus, it is especially advantageous if one measuring element is additionally at least partially implemented as resistor track of the heating element and the temperature-measuring element.

Furthermore, it is advantageous if an evaluation device is provided, which determines a change in the current flow applied between the measuring electrodes of the measuring elements, or which determines the electrical resistance, taking the measuring temperature into account, and outputs the result as a measure for a particle concentration or a particle mass flow.

The sensor element or the method for operating such is advantageously suitable for monitoring the operating method of a diesel engine and for monitoring the reliability or the degree of loading of a particulate filter.

Four exemplary embodiments of a sensor element according to the present invention are represented in the drawing in schematically simplified form and explained in greater detail in the following description.

BRIEF DESCRIPTION OF THE DRAWINGS

FIG. 1 shows an exploded view of a sensor element according to a first exemplary embodiment.

FIG. 2 shows the wiring of a temperature-measuring element integrated into a sensor element according to FIG. 1.

DETAILED DESCRIPTION

Figure 3:
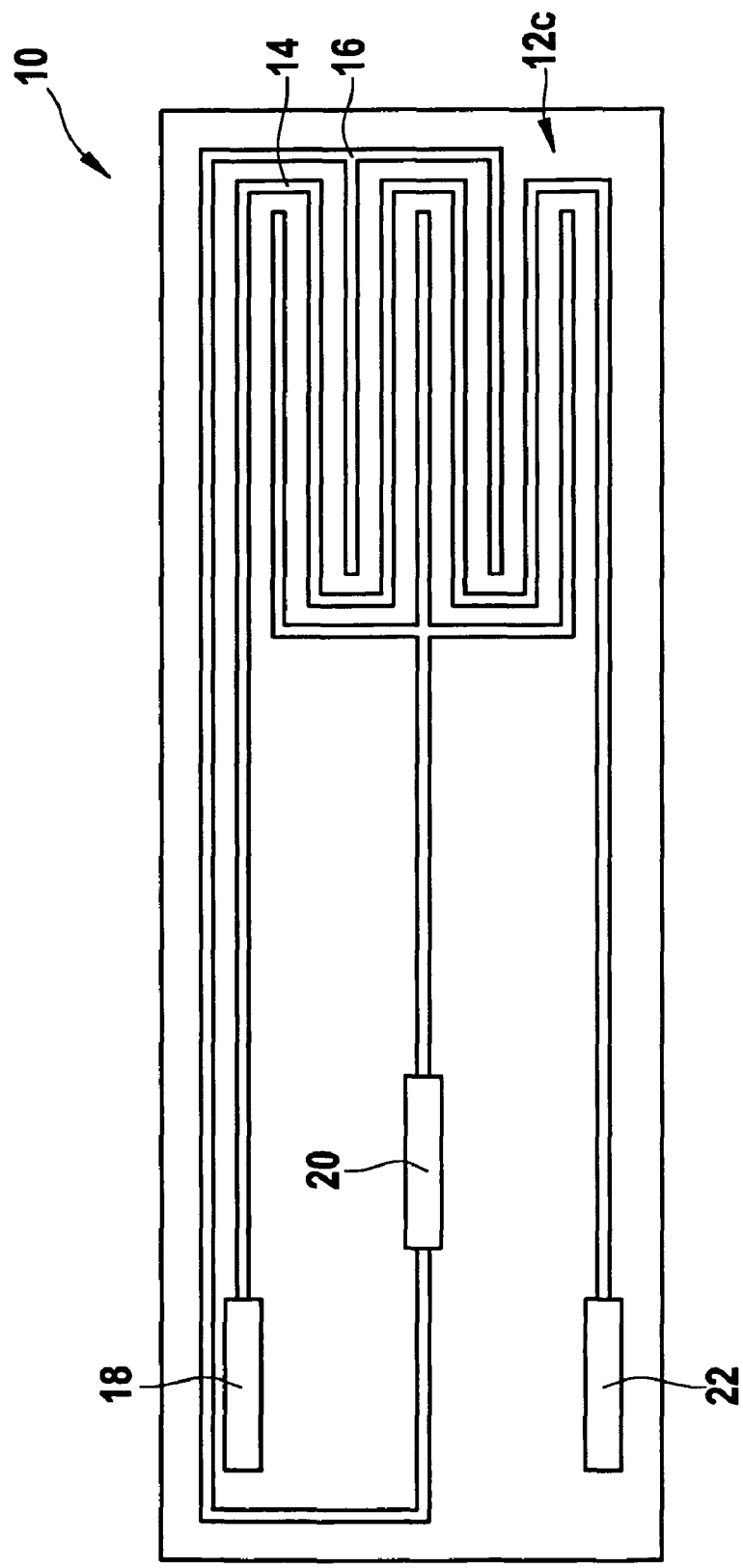
FIG. 3 shows a plan view of a section of a sensor element according to a second exemplary embodiment.

FIG. 1 shows a schematic of the structure of one specific embodiment according to the present invention. 10 denotes a ceramic sensor element, which is used to determine particles, such as soot particles, in a gas mixture surrounding the sensor element. Sensor element 10 includes, for example, a plurality of oxygen ion-conducting solid-state electrolyte layers $11a$, $11b$ and $11c$. In this context, solid-state electrolyte layers $11a$ and $11c$ are implemented as ceramic foils and make up a planar ceramic body. They may be made of an oxygen-ion-conducting solid-state electrolyte material such as $ZrO_2$ stabilized or partially stabilized by $Y_2O_3$.

In contrast, solid-state electrolyte layer 11b is produced by screen-printing a pasty ceramic material on solid-state electrolyte layer 11a, for example. The same solid-state electrolyte material as that of which solid-state electrolyte layers 11a, 11c are made of as well may be used as a ceramic component of the pasty material.

In addition, sensor element 10 has, for example, a multitude of electrically insulating ceramic layers 12a, 12b, 12c, 12d, 12e and 12f. Layers 12a-12f are likewise produced by screen printing a pasty ceramic material onto solid-state electrolyte layers 11a, 11c, for instance. Barium-containing aluminum oxide, for example, is used as the ceramic component of the pasty material in this instance, since it has an electric resistance that is constantly high for the most part, even under long-term, varying temperature stresses. Alternatively, the use of cerium dioxide or the addition of other earth alkali oxides is an option as well.

The integrated form of the planar ceramic body of sensor element 10 is produced by laminating together the ceramic foils printed over with solid-state electrolyte layer 11b and functional layers as well as layers 12a-12f, and by subsequently sintering the laminated structure in an available manner.

Moreover, sensor element 10 has a ceramic heating element 40, which is developed as an electric resistor track and is used to heat sensor element 10, particularly to the temperature of the gas mixture to be determined, and to burn off the soot particles deposited on the large surfaces of sensor element 10. Furthermore, the resistor track may be implemented in meander form and has plated through-holes 42, 44 at both ends, as well as electric contacts 46, 48. By applying an appropriate heating voltage to contacts 46, 48 of the resistor track, the heating output of heating element 40 is able to be regulated appropriately. The resistor track as well as contacts 46, 48 and plated through-holes 42, 44 may be made from a cermet material, which may be as a mixture of platinum and/or a platinum material having ceramic components, such as aluminum oxide, for instance.

On one large surface of sensor element 10, for example, two measuring electrodes 14, 16 are fixed in place, which may be implemented in the form of interdigital electrodes that are interleaved with one another and form an electrochemical measuring element. The use of interdigital electrodes as measuring electrodes 14, 16 advantageously allows an especially precise determination of the electric resistance and the electric conductivity of the surface material located between measuring electrodes 14, 16. For the contacting of measuring electrodes 14, 16, contacts 18, 20 are provided in the area of an end of the sensor element facing away from the gas mixture. The supply lead areas of electrodes 14, 16 are shielded from the effects of a gas mixture surrounding sensor element 10 which may be by an electrically insulating layer 12a. Measuring electrodes 14, 16 have an electrode cross section of 50 to 150 μm, for example. Like contacts 18, 20, for instance, as well, they may be made of platinum, rhodium, a platinum/rhodium alloy, or some other alloy exhibiting suitable electric conductivity. The electrode material of measuring electrodes 14, 16 is used in an available manner as cermet, in order to sinter the electrode material to the ceramic foils.

In addition, a porous cover or protective layer, which is not shown for reasons of clarity, may be provided on the large surface of sensor element 10 that is furnished with measuring electrodes 14, 16, which shields measuring electrodes 14, 16 in their interleaved area from direct contact with the gas mixture that is to be determined. The layer thickness of the porous protective layer in this instance may be greater than the layer thickness of measuring electrodes 14, 16. The porous protective layer may be implemented as open-pored layer, the pore size having been selected in such a way that the particles to be determined in the gas mixture are able to diffuse into the pores of the porous protective layer. The pore size of the porous protective layer may be in a range between 2 to 10 μm. The porous protective layer is developed of a ceramic material, which may be similar to the material of layer 12a, or is equivalent thereto, and may be produced by screen printing. The porosity of the porous protective layer is adjustable according to the requirements by the addition of pore-forming materials to the screen printing paste.

During the operation of sensor element 10, a voltage is applied to measuring electrodes 14, 16. Since measuring electrodes 14, 16 are situated on the surface of electrically insulating layer 12b, there is virtually no current flow between measuring electrodes 14, 16 initially.

If a gas mixture flowing around sensor element 10 contains particulate, especially soot, then it will deposit on the surface of sensor element 10. Since soot has a certain electric conductivity, if there is sufficient loading of the surface of sensor element 10 or the porous protective layer with soot, an increasing current flow, which correlates with the extent of the loading, will come about between measuring electrodes 14, 16.

If a constant DC or AC voltage is then applied to measuring electrodes 14, 16, and if the current flow passing between measuring electrodes 14, 16 is measured or the rise in the current flow is determined over the time, then it is possible to infer the deposited particle mass or the instantaneous particle mass flow, in particular the soot mass flow, and to infer the particle concentration in the gas mixture on the basis of the current flow or the differential quotient of the current flow over the time. As an alternative to the current flow, the electric resistance or the impedance between measuring electrodes 14, 16 may be taken into account. A calculation of the particle mass flow can be performed on the basis of the measured values, provided the flow rate of the gas mixture is known. This and the volume flow of the gas mixture are able to be determined by a suitable additional sensor, for example.

Furthermore, sensor element 10 includes a temperature-measuring element 30, which may be developed in the form of an electric resistor track. The resistor track is, for instance, made of a similar or the same material as the resistor track of heating element 40. The resistor track of temperature-measuring element 30 may be implemented in the form of a meander, and one of the connections of the resistor track may be connected to contact 18 via a plated contacting 19. Another electric connection of temperature-measuring element 30 may be in conductive connection to a further contact 22 via an additional plated contacting 21. By applying an appropriate voltage to connections 18, 22 of the resistor track, and by determining the electric resistance thereof, the temperature of sensor element 10 is able to be inferred.

The resistor track of temperature-measuring element 30 has a relatively low electric resistance of up to 180 Ohm, in particular of 80 to 120 Ohm, at a temperature of 0° C. But when utilized in ceramic gas sensors, the use of temperature-measuring elements whose resistor track has an electric resistance of at least 200 Ohm at 0° C. is common. However, the production of such resistor tracks requires special techniques of applying the material of the resistor track, for example thin-film technology, as it is generally understood, in which the applied conductor tracks are subsequently subjected to photo-fine structuring in order to be able to realize the relatively small conductor cross sections of the resistor tracks.

The use of a temperature-measuring element 30 whose resistor track exhibits an electric resistance of less than 180

Ohm at 0° C. makes it possible to produce the resistor track by thick-film technology, for instance by screen printing using a printing paste that contains the material of the resistor track. Since the resistor track of heating element 40 is realizable in the same way, additional synergy effects are derived thereby.

For instance, the resistor track of temperature-measuring element 30 has a conductor-track cross section of 100 to 130 µm and/or a spacing between the individual meander loops of the resistor tracks of 110 to 150 µm.

FIG. 2 illustrates the wiring of a temperature-measuring element 30 integrated into sensor element 10 by way of example. The resistor track of temperature-measuring element 30 constitutes a temperature-measuring resistor $R_T$, which forms an overall resistance together with a pre-resistor $R_V$. A voltage $U_B$ of 5 V present at the engine control device, for example, is applied there as operating voltage. Temperature-measuring resistor $R_T$ and pre-resistor $R_V$ constitute a voltage divider whose output voltage forms measuring voltage $U_M$. Measuring voltage $U_M$ may be applied to an A/D converter 24, for example. Measuring voltage $U_M$ is a measure for the electric resistance of temperature-measuring resistor $R_T$. The signal generated with the aid of A/D converter 24 may, for instance, be transmitted to an evaluation unit (not shown), which is integrated in a gas sensor that includes sensor element 10. Pre-resistor $R_V$ may likewise be part of the evaluation unit or the gas sensor.

Another specific embodiment is shown in FIG. 3, in which identical reference numerals denote the same components as in FIGS. 1 and 2.

Sensor element 10 according to the second specific embodiment is equipped with a first measuring electrode 14, which is simultaneously at least partially implemented as resistor track of temperature-measuring element 30. For this purpose, in addition to contact 18, first measuring electrode 14 also includes additional contact 22, and the electric resistance between contacts 18, 22 is utilized to determine the temperature, and the electric resistance between contacts 18, 20 is utilized to determine the particle loading.

As an alternative thereto, first measuring electrode 14 simultaneously may be at least partially implemented in the form of a resistor track of heating element 40. To this end, a heating voltage is applied to contacts 18, 22 for heating sensor element 10.

Figure 4:
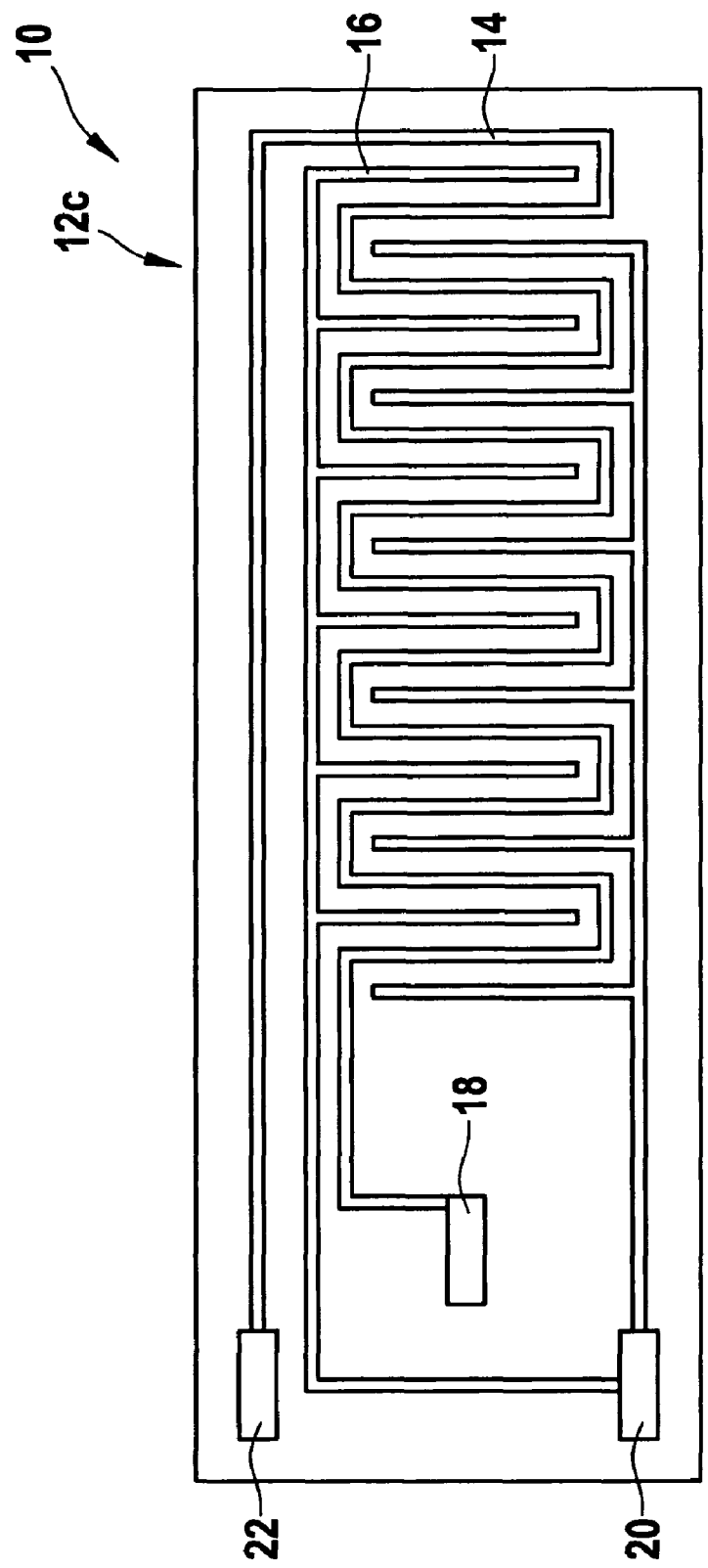
FIG. 4 shows a plan view of a section of a sensor element according to a variant of the exemplary embodiment illustrated in FIG. 3.

FIG. 4 shows a sensor element according to one variant of the sensor element shown in FIG. 3. As before, identical reference numerals denote the same components as in FIGS. 1 through 3. The arrangement of the meander structure made up of measuring electrodes 14, 16 has been rotated by 90°, so that a larger number of meander loops is able to be placed on ceramic layer 12b.

Figure 5:
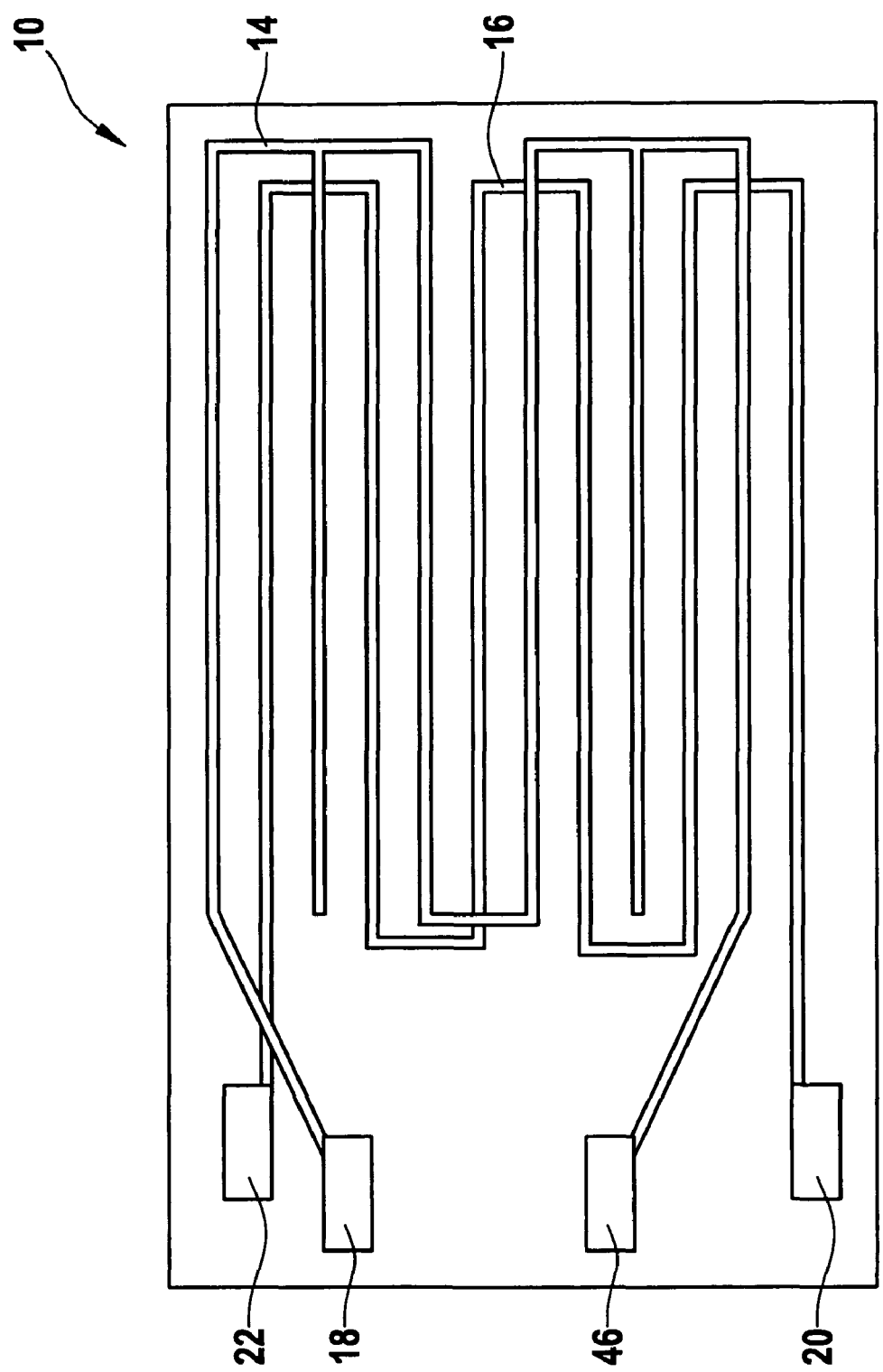
FIG. 5 shows a plan view of a section of a sensor element according to a third exemplary embodiment.

FIG. 5 shows a sensor element according to a third exemplary embodiment. Once again, identical reference numerals denote the same components as in FIGS. 1 through 4.

Sensor element 10 shown in FIG. 5 includes measuring electrodes 14, 16, which are disposed in different layer planes of the sensor element. For example, measuring electrode 14 is situated on a large surface of sensor element 10, which may be on ceramic layer 12b, which is porous in this exemplary embodiment and not shown in FIG. 5 for reasons of clarity. Measuring electrode 14 is contacted by contacts 18, 46. In an additional layer plane of sensor element 10, which may be between ceramic layers 12b and a further ceramic layer, which is not shown and is situated between ceramic layer 12b and solid-state electrolyte layer 11a, additional measuring electrode 16 is provided, which is connected to contacts 20, 22 via through-hole platings, which are not depicted.

To determine particles in the gas mixture to be examined, a current flow that occurs between contacts 18, 20 is determined, or an electric resistance, applied between these contacts, of ceramic layer 12b. Measuring electrode 14 situated on the large surface of sensor element 10 may be also used as resistor track of heating element 40. To this end, an appropriate heating voltage is intermittently applied to contacts 18, 46.

Further electrode 16 may additionally also be utilized as resistor track of temperature-measuring element 30. For this purpose the electric resistance of measuring electrode 16 at contacts 20, 22 is determined. Alternatively it is possible to implement first measuring electrode 14 as temperature-measuring element 30 and second measuring electrode 16 as heating element 40. Furthermore, more than one intermediate layer may be provided between measuring electrodes 14, 16.

An alternative method of operating measuring electrodes 14, 16 is to operate both as resistor track of a temperature-measuring element 30 during a first time period, in which measuring electrodes 14, 16 may be connected in series through a conductive connection of contacts 22, 46, and in which the electric overall resistance present at contacts 18, 20 is determined. In a second time period, measuring electrodes 14, 16 are then operated as heating elements, for which purpose a suitable heating voltage is applied to contacts 18, 46, and 20, 22. In a third time period, measuring electrodes 14, 16 are either operated for the measurement of a particle concentration, during which an electric current flow or an electric resistance between contacts 18, 20 is determined, or the measurement is carried out in the first or second time period in addition.

Figure 6:
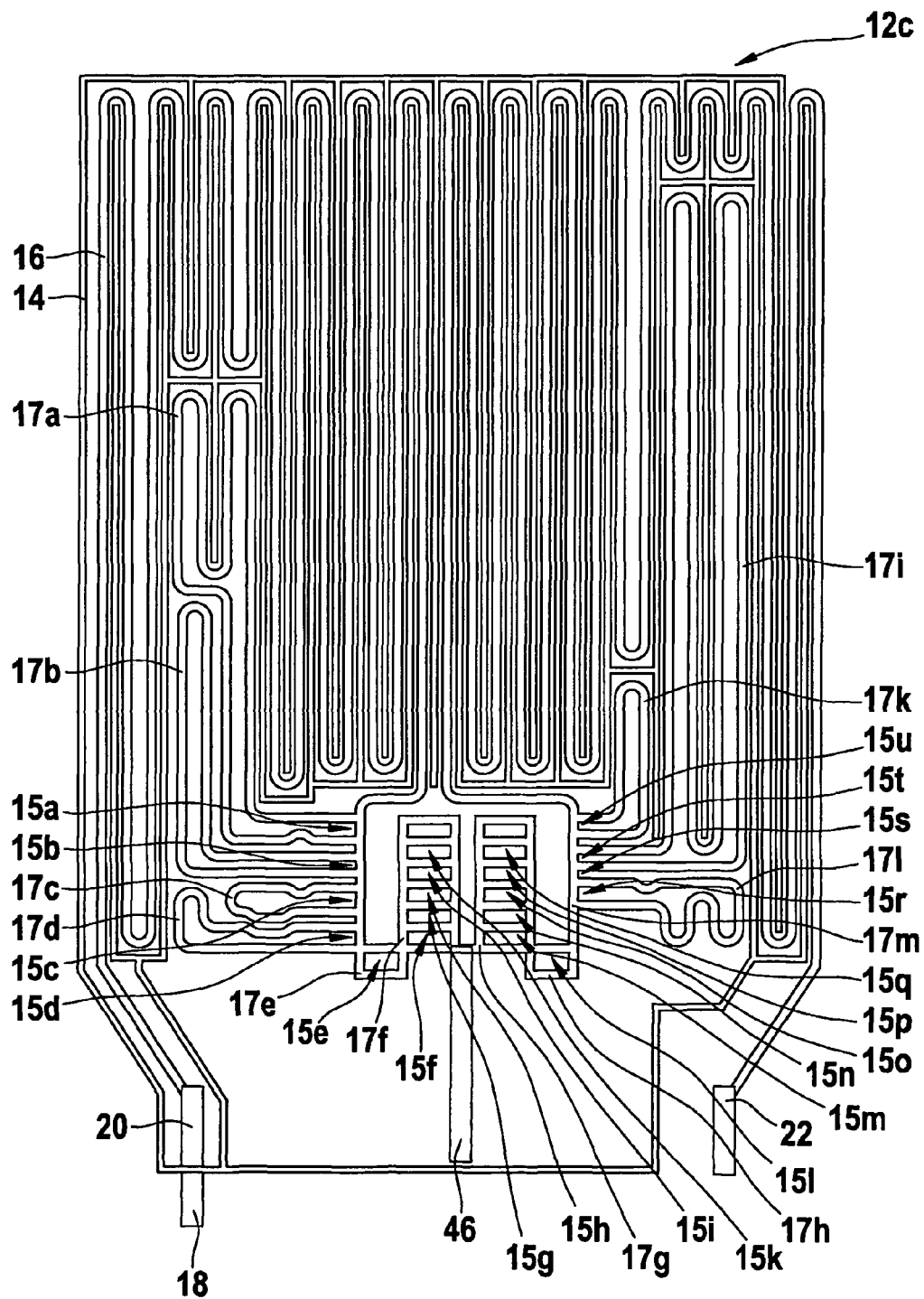
FIG. 6 shows a plan view of a section of a sensor element according to a fourth exemplary embodiment.

FIG. 6 shows a sensor element according to another exemplary embodiment. Once again, identical reference numerals denote the same components as in FIGS. 1 through 5.

According to this specific embodiment, further measuring electrode 16 of sensor element 10 is simultaneously implemented as resistor track of a temperature-measuring and a heating element 30, 40, respectively. In order to be able to precisely adjust the electric resistance of additional measuring electrode 16, which functions as resistor track, it includes meander loops 17a, 17b, 17c, 17d, 17e, 17f, 17g, 17h, 17i, 17k, 17l, 17m, which are bridged by burn-up segments 15a, 15b, 15c, 15d, 15e, 15f, 15g, 15h, 15i, 15k, 15l, 15m, 15n, 15o, 15p, 15q, 15r, 15s, 15t, 15u and which, following the production of the sensor element, are able to be burned off or interrupted, if necessary, via an appropriate energy supply. In this manner, by shortening the resistor track, its electric resistance is able to be adjusted to a desired value. The number and the design of meander loops 17a-17k as well as their implementation with regard to length and cross section is not fixedly specified and is modifiable. The same applies to burn-up segments 15a-15t.

During operation, an electric resistance between measuring electrodes 14, 16 at contacts 18, 20 and 18, 22 is determined in order to ascertain particles in the gas mixture; if necessary, the temperature is determined in addition, with the aid of a resistance measurement at contacts 20, 22, or a heating voltage is applied to contacts 20, 46 and 22, 46. In order to be able to provide an adequate heating output, a section of additional measuring electrode 16, such as the region between contacts 20 and 46 or between contacts 22 and 46, may be implemented with a larger line cross section, or it may contain a platinum/rhodium alloy, so that an electric overall resistance of these electrode regions of 10 to 50 results, in particular 10 Ohm.

The exemplary embodiments and/or exemplary methods of the present invention is not restricted to the specific embodiments of a sensor element shown in FIGS. 1 and 6, but allows numerous modifications of this sensor element to be undertaken. Thus, it is possible, for example, to provide additional ceramic layers in the sensor element or to simplify the multi-layer construction of the sensor element according to the application, as well as to provide additional measuring electrodes. The use of a plurality of heating elements and temperature-measuring elements is also a possibility.

The use of the sensor element described is not restricted to the determination of soot particles in exhaust gases of internal combustion engines, but it may be used quite generally for the determination of the concentration of particles that change the electric conductivity of a ceramic substrate when collecting, for instance in chemical production processes or in exhaust-air aftertreatment systems.

Furthermore, the exemplary embodiments and/or exemplary methods of the present invention is transferable to all ceramic sensor elements that are used to determine gases in gas mixtures and which include an integrated temperature-measuring element, such as oxygen, nitrogen oxide and ammonia sensors.

What is claimed is:

1. A sensor element for determining particles in a gas mixture, comprising:
    at least one electrochemical measuring element exposed to the gas mixture to be determined; and
    at least one temperature-measuring element integrated in the sensor element, wherein the temperature-measuring element includes a resistor track, which has an electric resistance of less than 180 Ohm at 0° C.;
    wherein the measuring element is a resistive measuring element and includes a first measuring electrode and a second measuring electrode;
    wherein at least one of (a) the first measuring electrode is at least partially implemented as the resistor track of the temperature-measuring element and a heating element, and (b) the second measuring electrode is at least partially implemented as the resistor track of the heating element.

2. The sensor element of claim 1, wherein the first and second measuring electrodes include interdigital electrodes.

3. The sensor element of claim 1, wherein the measuring electrodes are disposed in different layer planes of the sensor element.

4. The sensor element of claim 1, wherein the sensor element is configured to monitor at least one of a process of operation of a diesel engine, a reliability of a particle filter, and a loading state of the particle filter.

5. A sensor element for determining particles in a gas mixture, comprising:
    at least one electrochemical measuring element exposed to the gas mixture to be determined; and
    at least one temperature-measuring element integrated in the sensor element, wherein the temperature-measuring element includes a resistor track, which has an electric resistance of less than 180 Ohm at 0° C.;
    wherein the resistor track of the temperature-measuring element has conductor track regions bridged by burn-up segments.

6. A method for determining particles in a gas mixture, the method comprising:
    using a sensor element for determining the particles in the gas mixture, the sensor element including:
        at least one electrochemical measuring element exposed to the gas mixture to be determined; and
        at least one temperature-measuring element integrated in the sensor element, wherein the temperature-measuring element includes a resistor track, which has an electric resistance of less than 180 Ohm at 0° C.;
    wherein the measuring element is a resistive measuring element and includes a first measuring electrode and a second measuring electrode;
    wherein at least one of (a) the first measuring electrode is at least partially implemented as the resistor track of the temperature-measuring element and a heating element, and (b) the second measuring electrode is at least partially implemented as the resistor track of the heating element; and
    applying a voltage to at least two measuring electrodes;
    determining at least one of current flow between the measuring electrodes and electric resistance as a measure for at least one of the particle concentration and the particle mass flow; and
    outputting the measure.

7. The method of claim 6, wherein at least one of a process of operation of a diesel engine, a reliability of a particle filter, and a loading state of the particle filter is monitored.

8. The method of claim 6, wherein the particles include soot particles and the gas mixture includes exhaust gases of an internal combustion engine.

9. A method for determining particles in a gas mixture, the method comprising:
    using a sensor element for determining the particles in the gas mixture, the sensor element including:
        at least one electrochemical measuring element exposed to the gas mixture to be determined; and
        at least one temperature-measuring element integrated in the sensor element, wherein the temperature-measuring element includes a resistor track, which has an electric resistance of less than 180 Ohm at 0° C.;
    applying a voltage to at least two measuring electrodes;
    determining at least one of current flow between the measuring electrodes and electric resistance as a measure for at least one of the particle concentration and the particle mass flow; and
    outputting the measure;
    wherein the at least one of the current flow between the measuring electrodes and the electric resistance is correlated with a temperature determined with the temperature-measuring element of the sensor element, and wherein the measure for the at least one of the particle concentration and the particle mass flow is determined by evaluating a characteristics map in which a temperature dependency of the at least one of the current flow between the measuring electrodes and the electric resistance as a function of particle loading is stored.

10. A soot sensor for determining particles in a gas mixture, comprising:
    a sensor element for determining particles in a gas mixture, including:
        at least one electrochemical measuring element exposed to the gas mixture to be determined; and
        at least one temperature-measuring element integrated in the sensor element, wherein the temperature-measuring element includes a resistor track, which has an electric resistance of less than 180 Ohm at 0° C.;
    wherein the measuring element is a resistive measuring element and includes a first measuring electrode and a second measuring electrode;
    wherein at least one of (a) the first measuring electrode is at least partially implemented as the resistor track of the temperature-measuring element and a heating element, and (b) the second measuring electrode is at least partially implemented as the resistor track of the heating element; and an evaluation device to determine and store a correlation between a prevailing measuring temperature and at least one of a current flow between measuring electrodes of the sensor element and an electric resistance as a function of particle loading.

11. The gas sensor of claim 10, wherein the evaluation device, taking the measuring temperature into account, determines at least one of a current flow present between measuring electrodes of the sensor element, and a resistance or a change therein, and outputs it as a measure for at least one of the particle concentration and the particle mass flow.

12. The soot sensor of claim 10, wherein at least one of a process of operation of a diesel engine, a reliability of a particle filter, and a loading state of the particle filter is monitored.

* * * * *